(12) United States Patent
Bartoli

(10) Patent No.: US 7,887,531 B2
(45) Date of Patent: Feb. 15, 2011

(54) EXCIMER LASER UNIT AND RELATIVE CONTROL METHOD FOR PERFORMING CORNEA ABLATION TO REDUCE PRESBYOPIA

(75) Inventor: Franco Bartoli, Turin (IT)

(73) Assignee: Carl Zeiss Meditec AG, Jena (DE)

( * ) Notice: Subject to any disclaimer, the term of this patent is extended or adjusted under 35 U.S.C. 154(b) by 1095 days.

(21) Appl. No.: 10/535,617

(22) PCT Filed: Nov. 18, 2003

(86) PCT No.: PCT/IT03/00747

§ 371 (c)(1),
(2), (4) Date: Feb. 6, 2006

(87) PCT Pub. No.: WO2004/052253

PCT Pub. Date: Jun. 24, 2004

(65) Prior Publication Data

US 2006/0195074 A1   Aug. 31, 2006

(30) Foreign Application Priority Data

Nov. 19, 2002   (IT)   .......................... TO2002A1007

(51) Int. Cl.
*A61B 18/18* (2006.01)
(52) U.S. Cl. .......................................... 606/5; 351/212
(58) Field of Classification Search ................ 128/898; 351/212

See application file for complete search history.

(56) References Cited

U.S. PATENT DOCUMENTS

| | | | | |
|---|---|---|---|---|
| 5,777,719 A | * | 7/1998 | Williams et al. ............ 351/212 |
| 6,045,578 A | * | 4/2000 | Collins et al. ............... 623/4.1 |
| 6,050,687 A | * | 4/2000 | Bille et al. .................... 351/212 |
| 6,086,204 A | * | 7/2000 | Magnante .................... 351/212 |
| 6,155,684 A | * | 12/2000 | Bille et al. .................... 351/212 |
| 6,271,914 B1 | * | 8/2001 | Frey et al. .................... 356/124 |
| 6,280,435 B1 | * | 8/2001 | Odrich et al. .................. 606/5 |
| 6,511,180 B2 | * | 1/2003 | Guirao et al. ............... 351/211 |
| 6,561,648 B2 | * | 5/2003 | Thomas ....................... 351/221 |
| 6,663,619 B2 | * | 12/2003 | Odrich et al. .................. 606/5 |
| 2001/0053906 A1 | * | 12/2001 | Odrich et al. .................. 606/5 |
| 2006/0235369 A1 | * | 10/2006 | MacRae et al. ............... 606/4 |

* cited by examiner

*Primary Examiner*—Henry M Johnson, III
*Assistant Examiner*—Jeffrey B Lipitz
(74) *Attorney, Agent, or Firm*—Frommer Lawrence & Haug LLP

(57) ABSTRACT

There are described an excimer laser unit and a method of controlling the unit to perform cornea ablation to reduce presbyopia, wherein the excimer laser unit is controlled to form on the cornea a photoablative pattern inducing a fourth-order ocular aberration, in particular a positive spherical aberration. More specifically, an aberrometric map of the eye is first acquired indicating the visual defects of the eye, which include second-order visual defects such as hypermetropia, astigmatism, and myopia, and higher-order visual defects such as spherical aberration; if the detected spherical aberration is negative, it is reduced by numerically increasing its absolute value to obtain an overcorrect photoablative inducing positive spherical aberration; conversely, if the detected spherical aberration is positive, its sign is changed and its absolute value increased numerically to obtain an overcorrect photoablative pattern inducing positive spherical aberration; and the photoablative pattern so generated is supplied to the excimer laser unit for implementation on the cornea.

8 Claims, 9 Drawing Sheets

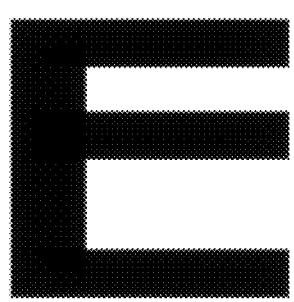
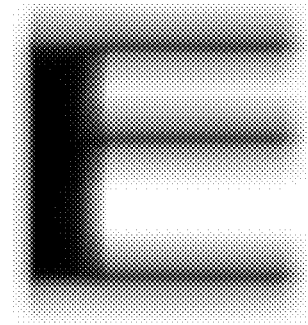
Fig. 4a        Fig. 4b
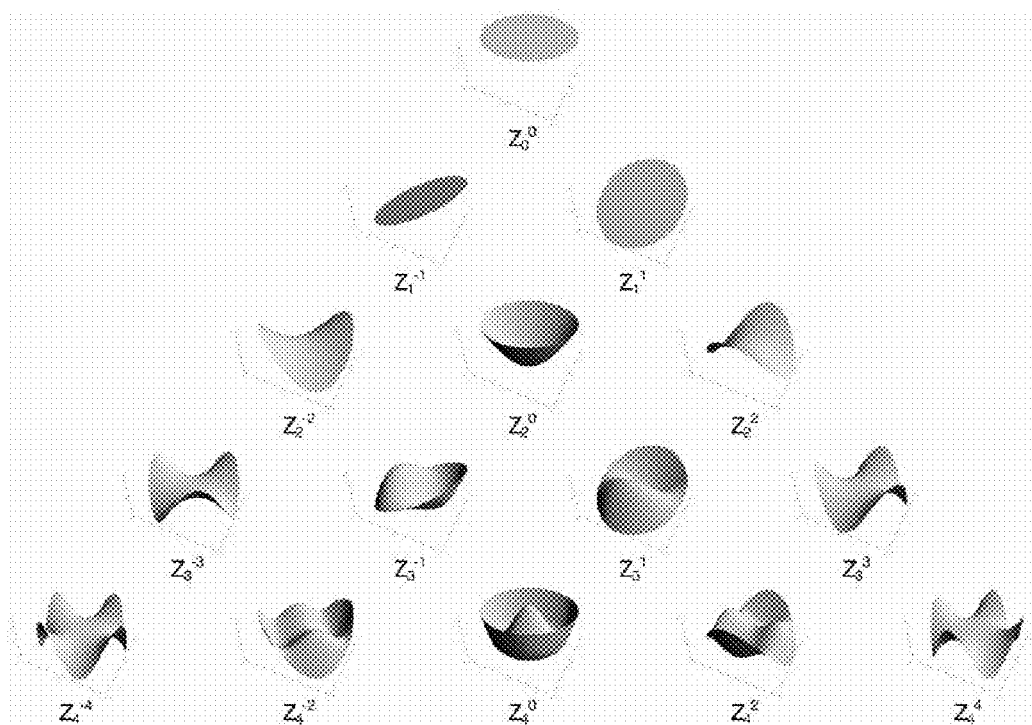
Fig. 5

| Term | Order | Polar form | Cartesian form | Description |
|---|---|---|---|---|
| $Z_0^0$ | 0 | 1 | 1 | |
| $Z_1^{-1}$ | 1 | $\rho \sin \Theta$ | X | inclination about the y axis |
| $Z_1^1$ | 1 | $\rho \cos \Theta$ | Y | inclination about the x axis |
| $Z_2^{-2}$ | 2 | $\rho^2 \sin 2\Theta$ | 2xy | astigmatism with axis a ± π/4 |
| $Z_2^0$ | 2 | $2\rho^2 - 1$ | $-1+2x^2+2y^2$ | focus translation |
| $Z_2^2$ | 2 | $\rho^2 \cos 2\Theta$ | $-x^2+y^2$ | astigmatism with axis at 0 or π |
| $Z_3^{-3}$ | 3 | $\rho^3 \sin 3\Theta$ | $-x^3+3xy^2$ | triangular astigmatism with base on the x axis |
| $Z_3^{-1}$ | 3 | $(3\rho^3 - 2\rho)\sin \Theta$ | $-2x +3x^3+3xy^2$ | third order coma along the x axis |
| $Z_3^1$ | 3 | $(3\rho^3 - 2\rho)\cos \Theta$ | $-2y +3x^2y+3y^3$ | third order coma along the x axis |
| $Z_3^3$ | 3 | $\rho^3 \cos 3\Theta$ | $-3x^2y+y^3$ | triangular astigmatism with base on the y axis |
| $Z_4^{-4}$ | 4 | $\rho^4 \sin 4\Theta$ | $-4x^3y+4xy^3$ | |
| $Z_4^{-2}$ | 4 | $(4\rho^4 - 3\rho^2)\sin 2\Theta$ | $6xy +8x^3y+8xy^3$ | |
| $Z_4^0$ | 4 | $6\rho^4 - 6\rho^2 + 1$ | $1-6x^2-6y^2+6x^4+ +12x^2y^2+6y^4$ | spherical aberration |
| $Z_4^2$ | 4 | $(4\rho^4 - 3\rho^2)\cos 2\Theta$ | $3x^2-3y^2-4x^4+4y^4$ | |
| $Z_4^4$ | 4 | $\rho^4 \cos 4\Theta$ | $x^4-6x^2y^2+y^4$ | |

Fig. 6

|  | II order | III order | IV order |
|---|---|---|---|
|  |  |  | $Z_4^{-4}$: -0.188 |
|  |  | $Z_3^{-3}$: -0.185 |  |
|  | $Z_2^{-2}$: -0.722 |  | $Z_4^{-2}$: -0.112 |
|  |  | $Z_3^{-1}$: -0.746 |  |
|  | $Z_2^{0}$: -0.079 |  | $Z_4^{0}$: -0.873 |
|  |  | $Z_3^{1}$: -0.466 |  |
|  | $Z_2^{2}$: -0.254 |  | $Z_4^{2}$: -0.093 |
|  |  | $Z_3^{3}$: -0.035 |  |
|  |  |  | $Z_4^{4}$: 0.105 |
|  |  |  |  |

|   | 7 | |
|---|---|---|
| | quantity | value |
| 1 | sphere X | -0.30 d |
| | cylinder X | -0.50 d |
| | axis | 8° |
| 2 | pupil diameter | 3.59 mm |
| 3 | analysis diameter | 3.59 mm |
| 4 | Z(3, -3) | 0.061 μm |
| | Z(3, -1) | -0.143 μm |
| | Z(3, 1) | -0.096 μm |
| | Z(3, 3) | -0.059 μm |
| | Z(4, -4) | 0.047 μm |
| | Z(4, -2) | 0.007 μm |
| | Z(4, 0) | -0.048 μm |
| | Z(4, 2) | -0.017 μm |
| | Z(4, 4) | 0.002 μm |
| 5 | PV OPD | 2.08 μm |
| | RMS OPD | 0.45 μm |
| | PV OPD HC | 0.41 μm |
| | RMS OPD HC | 0.07 μm |
| 6 | x offset | -0.53 mm |
| | y offset | -0.83 mm |

Focal point of second
(i.e., horizontal)
meridian, perpendicular
to first meridian.

Focal point of
first (i.e., vertical)
meridian.

EXCIMER LASER UNIT AND RELATIVE CONTROL METHOD FOR PERFORMING CORNEA ABLATION TO REDUCE PRESBYOPIA

CROSS-REFERENCE TO RELATED APPLICATIONS

This application claims priority of International Application No. PCT/IT 2003/000747, filed Nov. 18, 2003 and Italian Application No. TO 2002A001007, filed Nov. 19, 2002, the complete disclosures of which are hereby incorporated by reference.

TECHNICAL FIELD

The present invention relates to an excimer laser unit and relative control method for performing cornea ablation to reduce presbyopia.

BACKGROUND ART

As is known, the human eye can be likened to a camera, in which the lens is defined by two lenses in turn defined by the cornea and the crystalline lens, the diaphragm by the pupil, and the film by the retina.

The lens focuses the rays from the outside world on the retina; the diaphragm expands and contracts to allow enough light into the eye to permit optimum operation of the retina with no glare phenomena; and the photosensitive film, defined by the retina, converts the light energy impressed on it into a visual message which is transmitted to the cortical centres for interpretation.

A basic characteristic of the eye as an optical system is its ability to accommodate, i.e. to adjust its characteristics to the distance of the object, so that the image is always formed on the retina.

The lens of the human eye, as stated, is a converging system formed by the association of various diopters, i.e. slightly curved spherical surfaces separating two mediums of different refraction indexes.

FIG. 1 shows a human eye; and FIG. 2 the human eye represented as an optical system, in which A indicates the cornea, B the aqueous humour, C the crystalline lens, D the vitreous body, and E the retina.

More specifically:
the first diopter is defined by the anterior surface of the cornea, which has a converging power of about 48 diopters (a diopter is the inverse of the focal distance expressed in meters);
the second diopter is defined by the posterior surface of the cornea, which has a diverging effect of about 5 diopters;
the third diopter is defined by the crystalline lens, which may be likened to a biconvex lens, in which the radius of curvature of the anterior surface is 10 mm, and that of the posterior surface 6 mm; the converging power of the lens various from about 19 to 33 diopters, depending on the curvature of the anterior surface of the crystalline lens;
alternating with the ocular diopters and the retina are the aqueous humour and the vitreous body, which have a refraction index of about 1.33.

Of the surface of the cornea as a whole, only the central area, known as the optical area and of about 4 mm in diameter, is normally used, and is defined by the opening of the pupil diaphragm.

Length is one of the three basic elements of the optical system of the eye, together with vertex power and the refraction index of the mediums.

In the emmetropic, i.e. normal, eye, the light rays of distant objects are focused exactly on the retina.

Myopia, astigmatism, and hypermetropia are defects of the optical system which result in the image not being focused correctly on the retina.

Refraction defects can be determined by various methods, and research and analysis of them has developed in recent years thanks to the use of aberrometry and advanced optical aberration measuring equipment known in medical circles as aberrometers.

In simple terms, aberration of a wavefront is a deviation of the analysed wavefront form from a geometrically perfect reference form.

Wavefronts are affected by the composition of the medium through which light travels, in that different mediums, e.g. glass, air, water or fabric, produce different light speeds. In mediums with a lower light speed (higher refraction index), the wavelength is lower, on account of the wavefront travelling more slowly.

FIG. 3a shows what happens to a spherical wavefront travelling through a perfect focusing lens with the focal point coincident with the excitation centre of the wave.

More specifically, once past the lens, the spherical wavefront flattens out; whereas any imperfection of the lens produces deviations in the flat wavefront behind the lens, as shown in FIG. 3b.

Aberrations of the eye are thought to be deviations of the wavefront issuing from the eye with respect to a flat wavefront. The light diffused at a given point on the retina acts as a point light source and produces a spherical wavefront. The situation is very similar to the one shown in FIGS. 3a and 3b. The cornea, crystalline lens, and vitreous body act as a focusing lens; and if the optical system of the eye were perfect (i.e. functioned like a perfect lens), the wavefront issuing from the eye would be flat.

Aberrations within the eye are caused by various factors, e.g. variations in density within various optical subsystems of the eye, irregular or deformed shape of the interfaces between different parts of the eye, etc., which produce local changes in the wavefront form with respect to a given optimum form.

Depending on the extent of it, aberration of the human eye may result in considerable loss of visual acuity, as shown by way of example in FIGS. 4a and 4b. More specifically, FIG. 4a shows the image actually observed by a patient; and FIG. 4b what the patient actually sees without any correction.

In ophthalmology, aberration is commonly measured using Zernike's polynomials, which give a mathematical presentation of the aberrant wavefront as the sum of coefficient-weighted elementary functions, i.e. geometrical figures expressed as polynomials as a function of (x, y).

The reason for this choice lies in Zernike's polynomials being commonly used to describe aberrations in optical systems.

Using the coefficients of Zernike's polynomials, the wavefront on the pupil can be represented as the following sum:

$$WR(x, y) = \sum_{n=0}\sum_{m=0} c_{nm} Z_{nm}(x, y)$$

where $Z_{nm}$ are Zernike's polynomials, and $c_{nm}$ are the respective reconstruction coefficients weighting each specific Zernike term. The coefficients are expressed in μm, and numbers n and m characterize each polynomial.

The extent to which the reconstructed wavefront WR(x, y) approximates the real wavefront increases alongside an increase in the order n considered in the series.

FIG. 5 shows the geometrical figures defined by Zernike's polynomials up to the fourth order.

The table in FIG. 6 shows the mathematical description of Zernike's polynomials up to the fourth order, and in particular shows, for each polynomial, the identification symbol ("term"), the order, the polar and Cartesian form, and a description of the type of aberration.

The Zernike terms in the table are shown in the notation commonly used in ophthalmology, i.e. $Z_n^{-\nu}$, which shows the contributing frequencies directly. The superscript is correlated simply with n and m by $\nu=2m-n$.

Aberrometry provides for measuring the two basic values used in ophthalmology to measure second-order refractive defects; the sphere S and the cylinder C, which are expressed in diopters. The calculation shown below, using second-order Zernike coefficients, is now the method most commonly used in optics, even though the values may differ slightly from those measured using other (e.g. refractometric) methods, which calculate an average of second-order aberrations (the most important) and higher-order aberrations (third, fourth and higher);

$S=+2c_2^0$ therefore corresponds to an aberration defined by the coefficient of Zernike's polynomial $Z_2^0$ (second order, symmetrical);

$C=\pm\sqrt{(c_2^{-2})^2+(c_2^2)^2}$ therefore corresponds to the root mean square of the coefficients of the two asymmetrical second-order Zernike polynomials.

One criterion by which to assess the total extent of aberration is the RMS (Root Mean Square) value, which provides for quantifying, and so comparing, aberrations obtained from different measurements and patients.

The RMS value calculation indicates how the reconstructed wavefront differs from a flat wave, with reference to the two-dimensional variance of the wavefront $\sigma^2$.

Variance of the wavefront is given by:

$$\sigma^2 = \frac{\iint (WR - \overline{WR})^2 dx dy}{\pi}$$

with integration to be performed in unit disk D $(x^2+y^2 \leq 1)$, and where $\overline{WR}$ represents the average wavefront determined, and WR the specimen wavefront.

Visual performance of the eye is currently acquired and diagnosed using a wavefront analyser, which performs a complete analysis of the refractive path of light inside the eye using a technique based on the Shack-Hartmann wavefront sensor to analyse the wavefront.

By way of example, FIG. 7 shows a wavefront analyser known in medical circles as a WASCA manufactured by Carl Zeiss Meditec AG.

As shown schematically in FIG. 8, when point light is directed onto the retina, the WASCA wavefront analyser breaks up the reflected wavefront to obtain highly accurate, practically instantaneous ocular aberration measurements.

The WASCA wavefront analyser was designed to simplify ocular aberration examination. The patient's eye is aligned directly in front of the examination window with the aid of a television camera image of the iris displayed on the screen; at which point, the measurement can be made using the aberrometer. Once the point is created on the retina, a light beam emerges from the eye, and travels through the optic train of the unit and directly onto the Shack-Hartmann sensor. This comprises an array of small lenses connected to a CCD television camera, and is sensitive to alterations in the slope of the wavefront; and the CCD image is sent to a computer for data acquisition, storage and processing.

Data is displayed in the form of coloured three- or two-dimensional wavefront aberration maps, i.e. a "height map" in μm.

Data acquisition using a Shack-Hartmann sensor takes only 13 msec, which safeguards against the slightest eye movement in the process.

FIG. 9 shows a three-dimensional example of a wavefront and ocular aberration measurement. More specifically, FIG. 9 shows the wavefront as it emerges from the cornea, and reconstructed by WASCA wavefront analyser data. The radial measurement of this wavefront is normalized with respect to the pupil radius, so that this wavefront corresponds with the size of the pupil.

The WASCA wavefront analyser employs two-dimensional wavefront representation with colour-coded height indications (green=same as the reference level; warm colours=reading; cold colours=dip), and supplies:

the coefficients of Zernike's polynomials to the fourth order;
the equivalent sphere and cylinder parameters; and
the root means square (RMS) value.

By way of example, FIG. 10 shows a two-dimensional representation of the wavefront, and the coefficients of Zernike's polynomials to the fourth order, as supplied by the WASCA wavefront analyser.

As shown in FIG. 10, the wavefront shows marked third- and fourth-order aberration, which could not be measured using conventional instruments.

FIG. 11 shows the aberration table supplied by a WASCA wavefront analyser, and which contains the following values calculated for each aberration (the numbers below correspond with those in the aberration table):

1. Second-order aberrations, i.e. sphere and cylinder, expressed in diopters.
2. Pupil diameter in mm, as measured by the wavefront analyser.
3. Analysis diameter in mm, for analysing wavefront data; may vary, with a maximum diameter limited by the pupil diameter.
4. Third- and fourth-order, so-called higher-order, aberrations.
5. Numbers describing aberrations of the eye:
   PV OPD: peak-valley optical path difference of the measured wavefront (original data) or of the wavefront reconstructed by all the Zernike terms up to the fourth order (database importation);
   RMS OPD: root mean square value of OPD (on the basis of Zernike's polynomials up to the fourth order);
   HO only indicates the respective values for higher-order aberrations; the selected correction terms are subtracted from the global wavefront before calculating the PV and RMS values (corresponding to the High-Order Aberration map in the wavefront section).
6. x, y coordinates of the centre of the pupil with respect to the centre of the wavefront sensor.

The parameters to be corrected so as to also simulate residual post-ablation aberration can be selected in the aberration table (middle column).

The aberrometric analysis is shown on the computer screen connected to the aberrometer in various ways, one of the most common of which combines the aberration table and the two-dimensional colour graphic shown in FIG. 10.

Refractive defects of the eye are corrected, or at least reduced, by subjecting the cornea to ablation by an excimer laser unit.

FIG. 12 shows, by way of example, a MEL 70 G-SCAN excimer laser unit manufactured by Carl Zeiss Meditec AG, which can be connected directly to the WASCA aberrometer of the same make.

The main commands for manual ablation control are entered via the keyboard and monitor with which the excimer laser unit is equipped.

The excimer laser and cornea tissue interact by the high-energy photons in the ultraviolet light of the laser breaking the intermolecular bonds. The uniqueness of excimer laser cornea ablation lies in individual photons having sufficient energy to break individual molecular bonds. The energy of a 193 millimicron laser light photon is much higher than that required to break molecular bonds, and the surplus energy serves to excite the fragments, and contributes in providing the kinetic energy to expel them from the surface. When energy intensity exceeds the ablation threshold, each laser light pulse removes a precise quantity of cornea tissue of uniform depth. Ablation depth depends on the amount of energy striking the cornea. The most effective energy intensity in ablation terms is 120-180 $mJ/cm^2$, and each spot removes $0.25\mu$ per pulse.

In excimer laser ablation, it is essential to obtain a smooth, uniform surface. Smoothness and uniformity are essential to maintain transparency of the cornea, and depend on two major factors: constant hydration of the stromal tissue, and homogeneity of the laser beam.

An excimer laser beam has two main characteristics: fluence and homogeneity, by which are meant, respectively, the amount of energy applied to the ablation area, and the energy distribution pattern within the ablation area.

More specifically, fluence is expressed in $mJ/cm^2$, and ranges from 100 to 230 $mJ/cm^2$, depending on the laser. Theoretically, an increase in fluence improves the quality of the beam, but also increases the heat effect and acoustic shock, and produces more rapid wear of the optical components of the laser.

The ablation rate (cut rate) is the amount of tissue removed per pulse, and depends on the characteristics of the tissue being treated. At cornea level, each layer of tissue has a different ablation rate, the average being calculated as $\sim0.25\mu$.

Each excimer laser unit has a definite beam shape or energy profile, which may be homogenous (top hat) or Gaussian, as shown in FIGS. 13a and 13b. The homogeneous profile has an equal energy distribution density, and is therefore square in shape, whereas the (bell-shaped) Gaussian profile has a higher density in the middle than at the periphery.

The profile of the laser beam issuing from the resonant cavity, in fact, is rectangular, and never homogeneous, i.e. has energy peaks of different intensity, so each excimer laser unit has a computer program (delivery system) for imparting a given profile and obtaining a homogenous laser beam.

The importance of the beam profile lies in radiation reproducing the shape of its energy profile directly on the cornea. In other words, the laser beam striking the cornea reproduces the shape of its profile as an impression on the cornea.

A non-homogeneous laser beam profile results in non-uniform ablation. So, to obtain a homogeneous profile, the laser beam is remodelled using lenses, mirrors, attenuators, prisms, and a prismatic integrator with a telescopic zoom.

More specifically, a homogeneous-profile (top hat) beam, with equal amounts of energy at the centre and periphery, removes a homogeneous amount of tissue, whereas a Gaussian-profile beam removes more tissue at the centre than at the periphery of the impact area.

Correction of refractive defects of the eye, be they spherical and/or cylindrical, call for specific photoablative patterns:
central flattening of the cornea for myopia: circular central ablation area;
central curving of the cornea for hypermetropia: peripheral circular corona ablation;
flattening and curving along only one meridian for astigmatism;
a combination of different photoablative patterns to correct spherical-cylindrical defects; and
customized photoablative patterns to correct asymmetrical or irregular or higher-order defects.

Geometric ablation figures must therefore be constructed on the cornea tissue, so as to only modify its refractive power in axial defects, and to modify its refractive power by rounding the surface in cylindrical defects. In asymmetrical or irregular defects, the photoablative pattern is guided by topography.

Using an excimer laser unit, sub-micron portions of cornea tissue can be removed extremely accurately to alter the curvature, and hence refractive power, of the cornea.

In 1988, Munnerlyn devised an algorithm relating ablation diameter and depth to required dioptric variance, and which allows control of an excimer laser unit on the basis of optical parameters (diopters) as opposed to geometrical parameters, thus greatly simplifying operation of the unit.

The laser beam generated by an excimer laser unit may be:
broad and circular (broad beam): this removes cornea tissue in concentric layers of varying diameter, and is suitable for constructing geometrically simple photoablative patterns (myopia):
slitted, in which the laser beam is diaphragmed to obtain a rectangular beam of variable size, which is distributed over the cornea by a linear or rotation system: this provides for constructing medium-simple photoablative patterns (myopia and myopic astigmatism);
a flying spot, in which a very small laser beam (1-2 mm) is used, and which removes a small patch of tissue at each spot. Correction is achieved by the laser spot scanning the cornea, and being passed several times where more material is to be removed. This system provides for constructing any photoablative pattern (geometric photoablative figure) and so correcting any ametropia of the eye.

The MEL 70 G-SCAN excimer laser unit mentioned above, for example, generates a 1.8 mm flying spot laser beam with a Gaussian profile for random circular scanning or random spot scanning ablation.

The following is a detailed analysis of each refractive defect of the eye and how it is corrected.

Hypermetropia is an extremely common refractive defect, so much so that, statistically, 53-56% of eyes are hypermetropic by 0.5 of a diopter or more.

In this defect, rays from an infinite distance are focused behind the retina, on account of the poor vertex power of the eye with respect to its length.

As opposed to a point image, a larger, blurred image is therefore formed on the retina, as shown in FIG. 14.

The defect is measured by the "sphere" parameter value, which is positive. To bring vision back to normal, the vertex power must be increased, which may be done partly by accommodation or totally in artificial manner with the aid of positive spherical lenses. The degree of hypermetropia is normally expressed by the power of the positive lens which, placed in front of the eye, focuses rays from an infinite distance on the retina.

The object in correcting a hypermetropic defect is to increase the vertex power of the cornea. Hypermetropic ablation aims at increasing the curvature of the central optical area of the cornea. Unlike myopic photoablation, the central portion of the cornea is practically left untreated, and is curved by removing the periphery.

A fairly large (5 mm) centrally curved optical area must therefore be obtained to also ensure good night vision. Fortunately, hypermetropes have a sufficiently small-diameter pupil. The circular corona treated area is located six to nine millimeters from the centre of the pupil. It is therefore an extensive excavation, with both central and peripheral transitions, to avoid sharp changes in curvature, which induce severe scarring processes.

It is essential not to induce a post-treatment increase in central curvature of over 50 diopters, which would result in a central keratoconus, with associated visual and central reepithelialization problems. Correctable hypermetropia is therefore limited (4-5 diopters): the flatter the original cornea, the greater the extent to which hypermetropia is correctable.

Myopia, on the other hand, is a refractive defect in which the relationship between eyeball length and vertex power is so altered that the vertex power is too great for the length of the eyeball, with the result that parallel rays striking the surface of the cornea are focused in front of the retina, as shown in FIG. 15.

In myopia, for the image of an object to be focused on the retina, the object must be placed at a finite distance, so that the rays from it diverge onto the surface of the cornea.

The defect is measured by the "sphere" parameter value, which is negative.

Myopia may be caused by:
a longer than normal eyeball (the most common cause);
greater than normal curvature of the cornea;
a greater than normal curvature of the anterior surface of the crystalline lens (as in accommodation spasm);
a crystalline lens too close to the cornea, i.e. a lower than normal anterior chamber;
a higher than normal refraction index of the crystalline lens core (as in initial cataract stages).

The object in correcting myopia is to reduce the vertex power of the cornea, which means reducing the curvature of, i.e. flattening, the central optical area of the cornea.

This is done by circular tissue ablation, which gets deeper as it gets larger.

The ablation area must be as large as possible, at least larger than projection of the pupil on the cornea, with a very gradual connection to the periphery, with no sharp variations in curvature; must maintain the original prolate profile (curving more at the centre than at the periphery); and must be as regular and smooth as possible. All these are necessary for acceptance and homogeneous coverage of the new surface of the cornea by the epithelium.

Finally, astigmatism is a refractive defect in which the diopter of the eye does not have the same refractive power in all meridians. Given a point source and a converging lens which does not have the same power in all meridians, a point image can never be formed. Instead, when the screen is moved back and forth, two lines, one perpendicular to the other and in different planes, will be focussed, as shown in FIG. 16.

The defect is measured by the "cylinder" parameter value, which is other than 0, and comes in two forms: regular astigmatism, in which curvature differs between one meridian and another, but is always the same along the same meridian; and irregular astigmatism, in which curvature differs at different points in the same meridian.

Ophthalmometric analysis of astigmatism gives the mean dioptric value of the two main cornea meridians in a 3 mm central area, thus characterizing astigmatism quantitatively (diopters) and qualitatively (regular or irregular) within the central area.

Topographical analysis, with a point by point evaluation of the radii of curvature over an extensive surface, enables morphological evaluation of the cornea from the refractive standpoint, and shows the cornea to be, not spherical, but aspherical: curving more at the centre, and flatter at the periphery.

The photoablative technique for correcting astigmatism, be it positive or negative, is based on applying a hypermetropic or myopic pattern to only one meridian, i.e. only one meridian is curved or flattened. The current tendency is for ablation in two planes of symmetry to modify above all the flatter meridian, and to remove tissue from the flatter meridian to bring it to the same curvature as the more curved meridian.

The widely varying morphology of astigmatism explains the difficulty encountered, in the early years of photoablation, in correcting it using excimer laser equipment with rigid ablation patterns. Only in recent years, in fact, has it been possible to adapt photoablation to topographical data (topographical link).

Correction of myopia, hypermetropia and astigmatism is based on laser ablation techniques employing photoablative patterns designed to eliminate the cylinder and sphere, i.e. to eliminate second-order aberrations.

Ablations can also be combined to eliminate in one pass both the sphere defect (myopia or hypermetropia) and the cylinder defect (astigmatism).

Higher-order aberrations are normally left unchanged. More specifically, third-order aberrations are normally associated with "coma" visual defects, while fourth-order aberrations, and particularly the spherical aberration measured by the coefficient of Zernike's polynomial $Z_4^0$, are partly related to transient accommodation phenomena.

By way of example, FIG. 17 shows the breakdown of an aberration into its second-order, i.e. cylinder and sphere, and higher-order components.

The WASCA aberrometer is able to isolate these aberrations and produce a particular photoablative pattern to specifically eliminate higher-order aberrations.

The photoablative pattern is generated electronically and sent directly to the excimer laser unit. The aberrometer can be adjusted to modify the coefficients of Zernike's polynomials to obtain special ablative patterns.

Presbyopia, on the other hand, is a visual defect which consists in diminished accommodation power of the eye to focus on near objects, is mainly encountered in adults, and is due to a loss of elasticity of the crystalline lens. Unlike myopia, hypermetropia and astigmatism, presbyopia is therefore not a refractive defect and, unlike the cases described above, is not easy to solve using photoablative techniques.

OBJECT AND SUMMARY OF THE INVENTION

It is a primary object of the present invention to provide an excimer laser unit and relative control method for performing cornea ablation to reduce presbyopia.

According to the present invention, there is provided a method of controlling an excimer laser unit to perform cornea ablation to reduce presbyopia.

The present invention also relates to an excimer laser unit for performing cornea ablation to reduce presbyopia.

BRIEF DESCRIPTION OF THE DRAWINGS

A non-limiting embodiment of the present invention will be described by way of example with reference to the accompanying drawings, in which:

FIGS. 4a and 4b show, respectively, an image observed by a patient with aberration of the eye, and what the patient actually sees with no correction;

FIG. 5 shows the geometrical figures defined by Zernike's polynomials to the fourth order;

FIG. 6 shows a table containing a mathematical description of Zernike's polynomials to the fourth order;

DESCRIPTION OF THE PREFERRED EMBODIMENTS

The present invention is the result of research conducted by the Applicant, and which has revealed that, unlike myopia, hypermetropia and astigmatism correction, in which laser ablation is aimed at eliminating second-order, i.e. cylinder and sphere, aberrations, presbyopia can be reduced by laser ablation of the cornea using a photoablative pattern which induces fourth-order, in particular positive spherical, ocular aberration.

Research by the Applicant, in fact, has revealed a relationship between the accommodation power of the eye and fourth-order, in particular spherical, aberrations. More specifically, research has shown that, during accommodation of the eye, a variation, in particular an increase, occurs in spherical aberration, which, from neutral or slightly negative, becomes positive.

As a result, it has now been determined that, in losing accommodation power with age, presbyopes lose the ability to induce spherical aberration.

The obvious conclusion to be drawn here is therefore the possibility of partly compensating for the loss of accommodation power of the presbyope by inducing an increase in spherical aberration.

Moreover, research has shown that correction of higher-order aberrations increases the visual capacity of the eye in the presbyope, and that combining an increase in spherical aberration with high-order aberration treatment therefore produces a significant improvement in near vision.

Spherical aberration can be induced using the same excimer laser unit as for myopia, hypermetropia and astigmatism correction, providing it is so controlled as to produce photoablative patterns specifically designed for the purpose.

The way in which the excimer laser unit is controlled to produce specific photoablative patterns to reduce presbyopia will be described below in detail with reference to the FIG. 18 flow chart.

Figure 1:
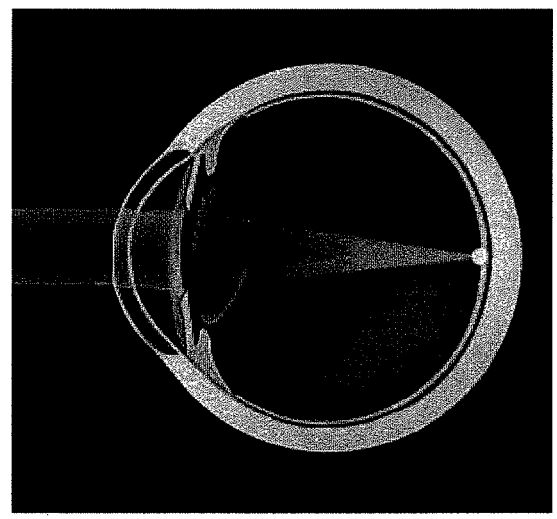
FIG. 1 shows a human eye.
Figure 2:
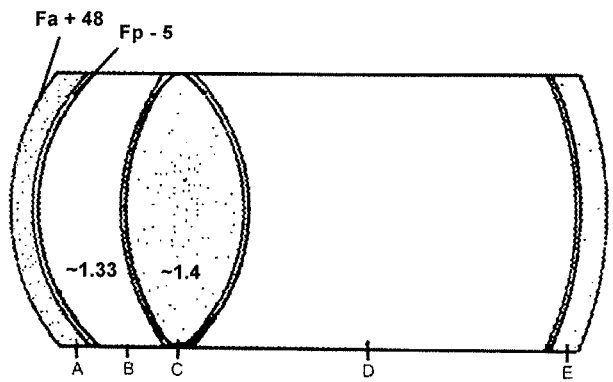
FIG. 2 shows the human eye as an optical system.
Figures 3A, 3B:
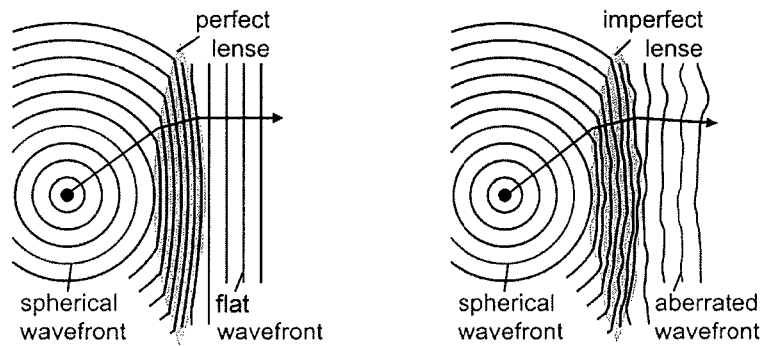
FIGS. 3a and 3b show what happens to a spherical wavefront travelling through a perfect focusing lens and an imperfect focusing lens respectively.
Figure 7:
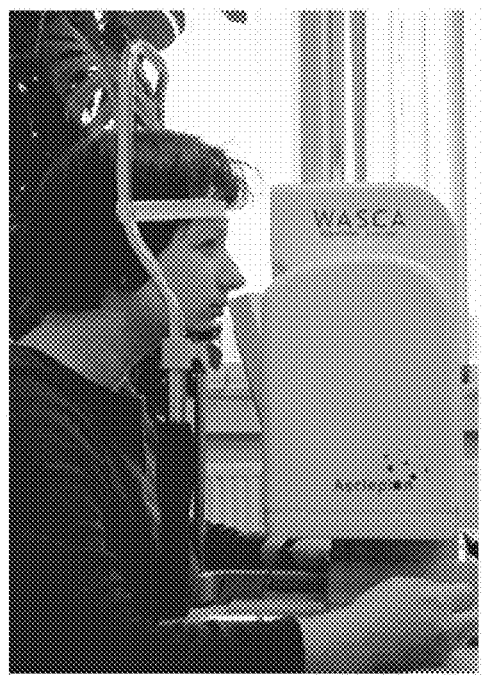
FIG. 7 shows a WASCA wavefront analyser.
Figure 8:
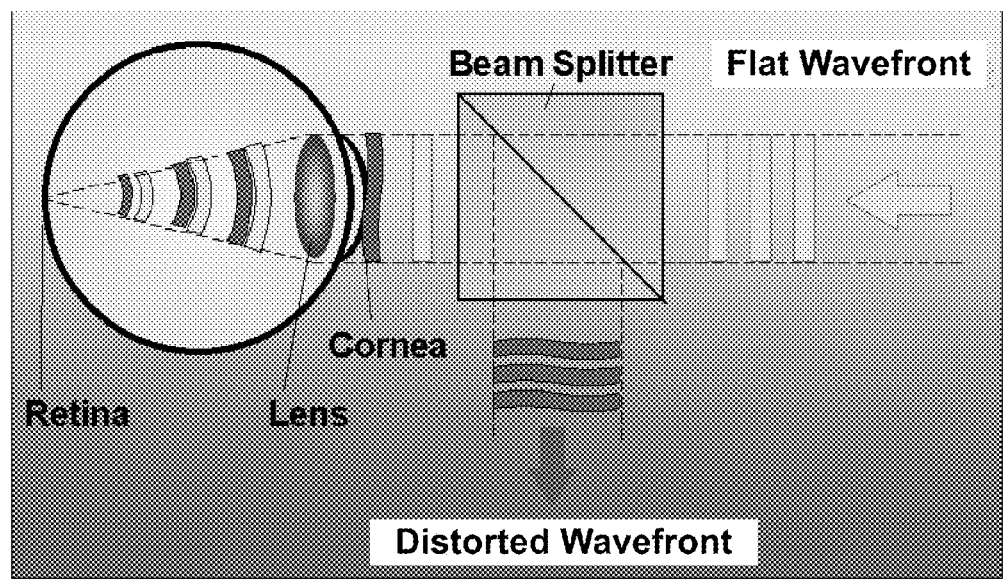
FIG. 8 shows, schematically, the operating principle of a WASCA wavefront analyser.
Figures 9, 10:
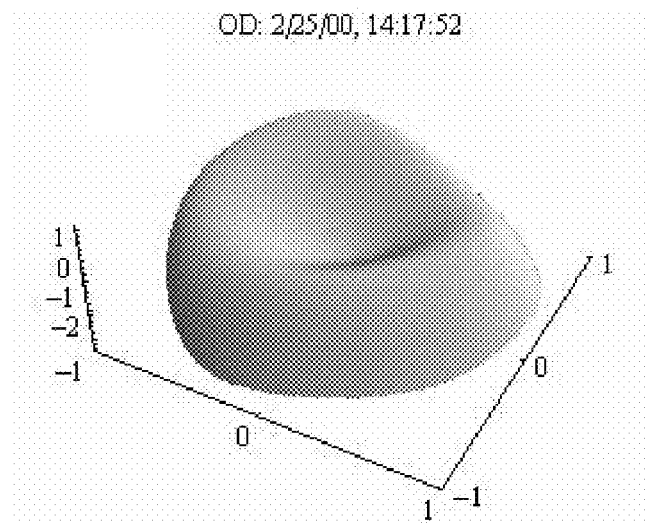
FIG. 9 shows a three-dimensional wavefront as it emerges from the cornea.
FIG. 10 shows a two-dimensional wavefront and the coefficients of Zernike's polynomials to the fourth order, as supplied by a WASCA wavefront analyser.
Figures 11, 12:
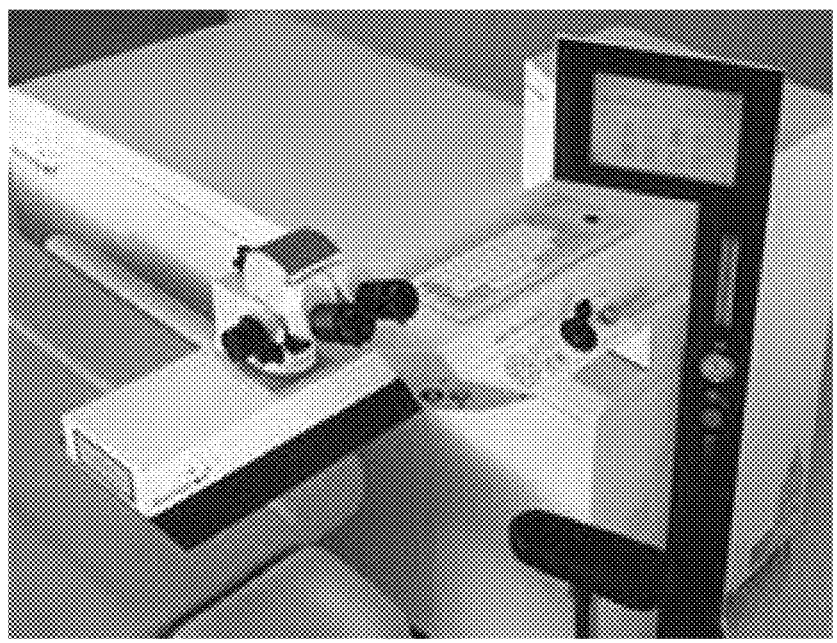
FIG. 11 shows the aberration table supplied by a WASCA wavefront analyser.
FIG. 12 shows an excimer laser unit.
Figure 13A:
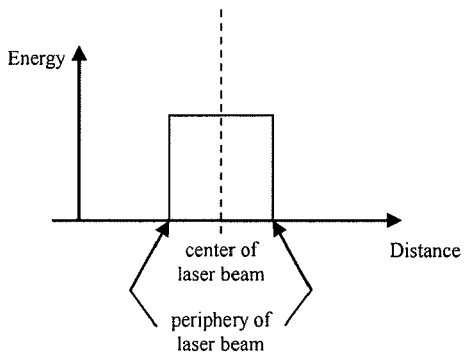
FIGS. 13a and 13b show a homogenous profile and a Gaussian profile respectively of a laser beam emitted by an excimer laser unit.
Figure 13B:
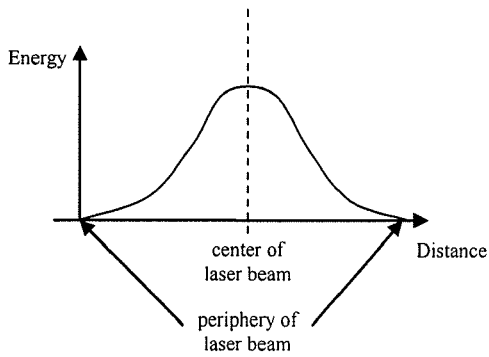
Figure 14:
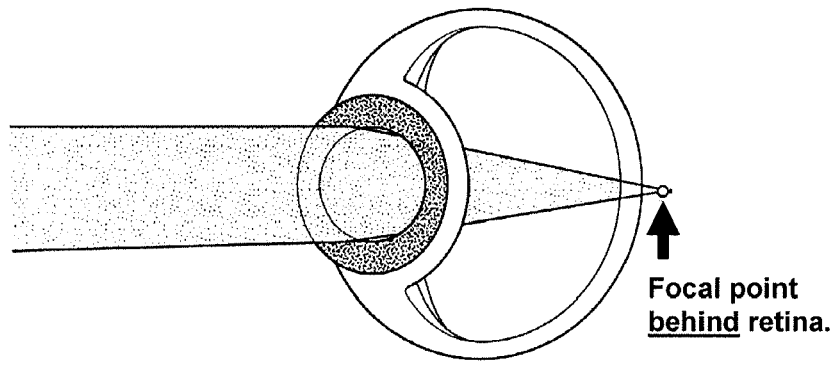
FIG. 14 shows the image formed on the retina of a hypermetropic eye.
Figure 15:
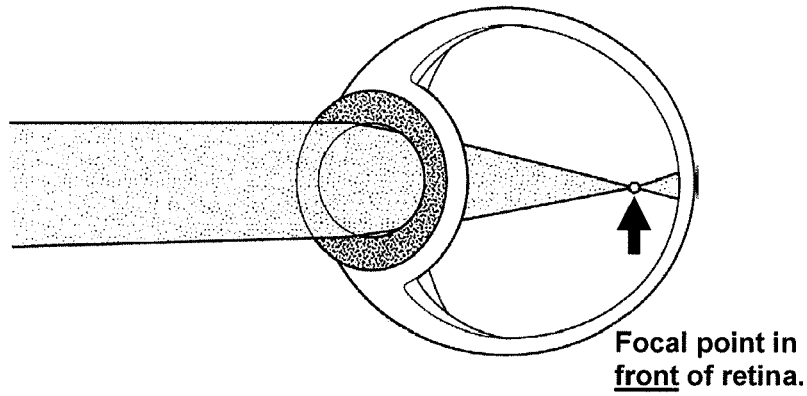
FIG. 15 shows the image formed on the retina of a myopic eye.
Figure 16:
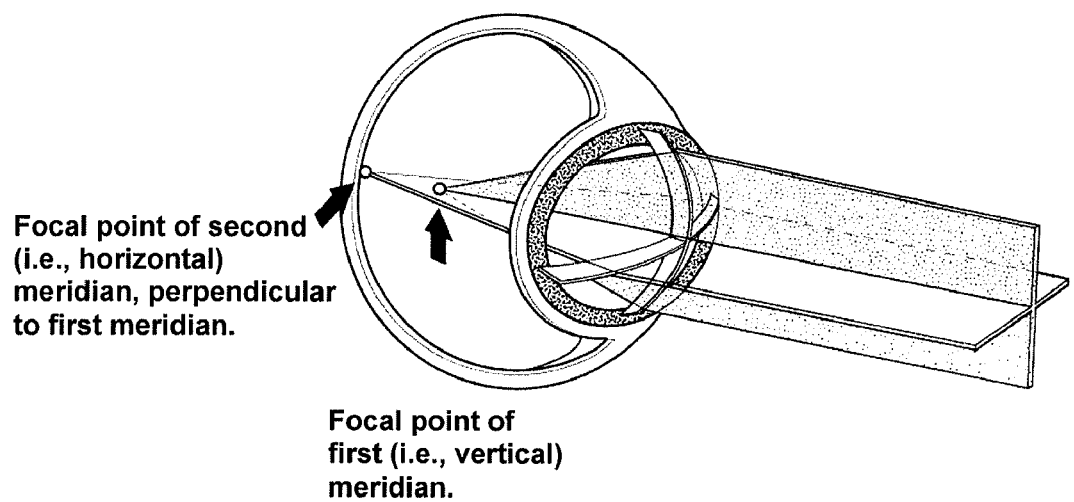
FIG. 16 shows the image formed on the retina of an astigmatic eye.
Figure 17:
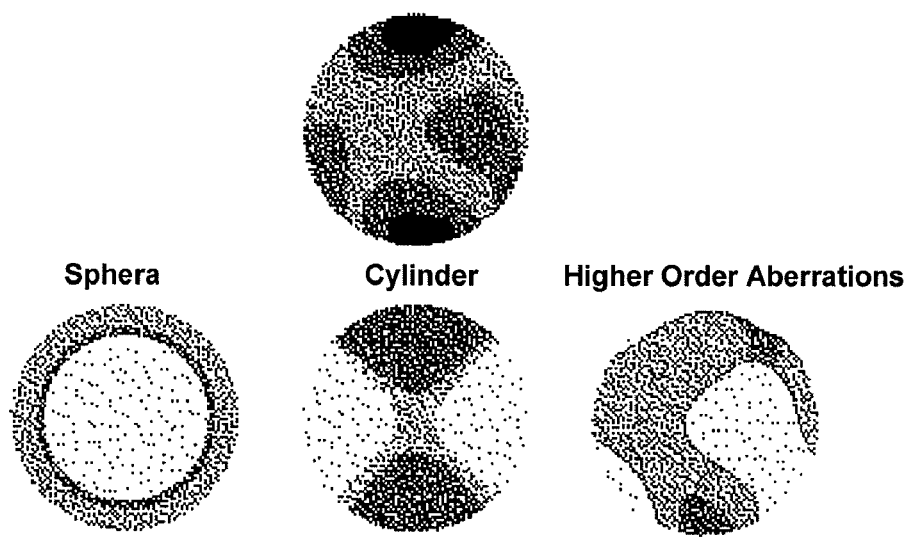
FIG. 17 shows the breakdown of a generic aberration into second- and higher-order components.
Figure 18:
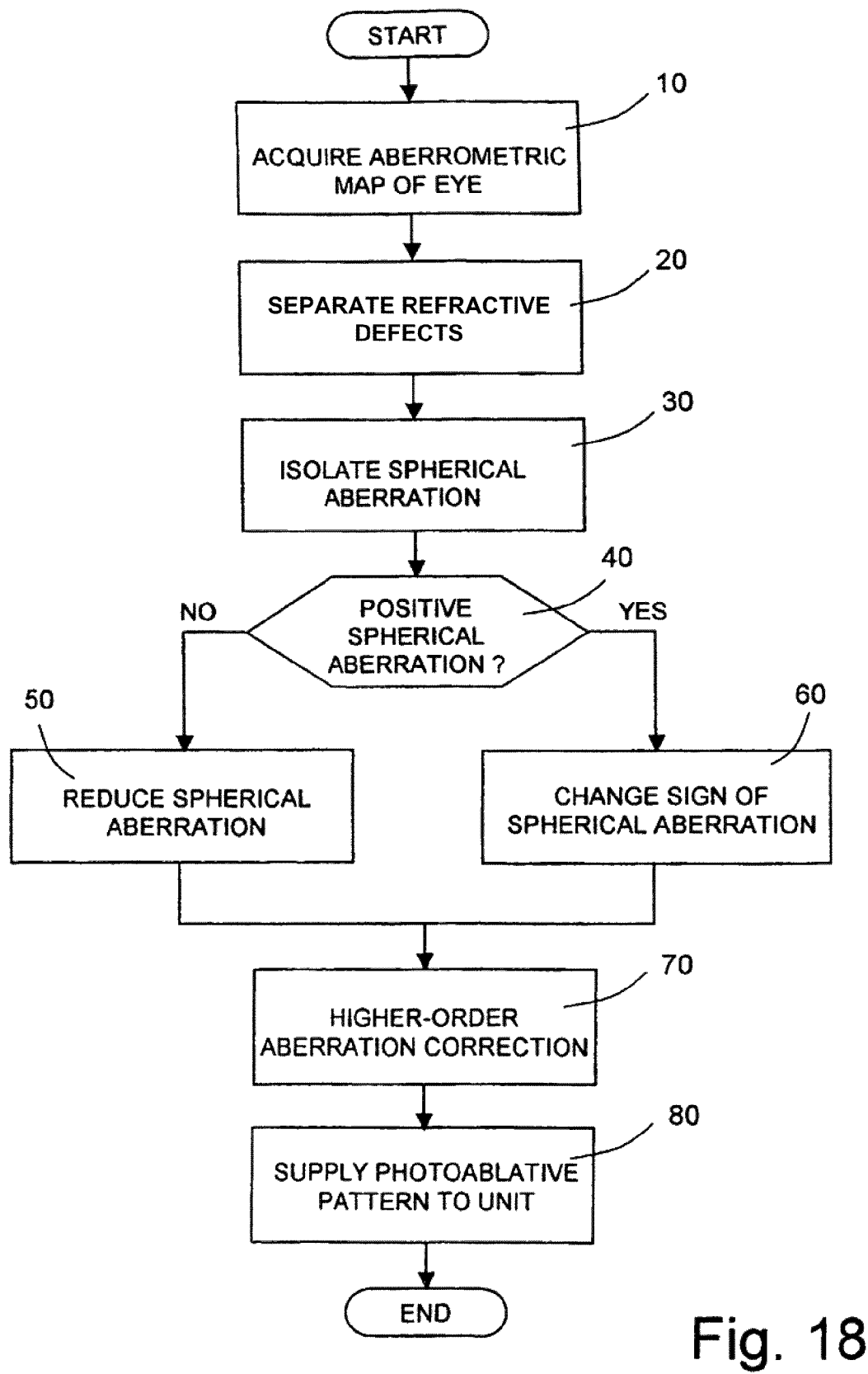
FIG. 18 shows a flow chart of the operations performed according to the method of the present invention.

As shown in FIG. 18, the first step is to acquire an aberrometric map of the eye, e.g. using the WASCA wavefront analyser described above (block 10).

The second step is to separate the low-order, i.e. sphere and cylinder, defects from the higher-order defects (block 20).

The third step is to isolate the detected spherical aberration (block 30).

The fourth step is to determine whether the detected spherical aberration is positive or negative (block 40).

If the detected spherical aberration is negative (NO output of block 40), it is reduced by numerically increasing its absolute value to obtain an overcorrect photoablative pattern and so induce positive spherical aberration (block 50).

Conversely, if the detected spherical aberration is positive (YES output of block 40), its sign is changed, and it is increased numerically in absolute value to obtain an overcorrect photoablative pattern and so induce positive spherical aberration (block 60).

Since, as stated, combining an increase in spherical aberration with high-order aberration treatment produces a significant improvement in near vision, the photoablative pattern so generated is further modified to also take corrections of higher than second-order aberrations into account (block 70).

The photoablative pattern is then sent to the excimer laser unit for the operation, and is implemented by the unit on the cornea in known manner not described in detail (block 80).

More specifically, as regards positive spherical aberration induction, the excimer laser unit must be controlled in a particular way, depending on the refractive defect associated with the presbyopia, as described below.

The starting point I the decision table shown below, which, depending on the second-order refractive defect associated with the presbyopia, indicates the ablative treatment required:

|   | Sphere | Cylinder | Defect | Treatment |
|---|--------|----------|--------|-----------|
| 1 | + | + | Hypermetropia and positive astigmatism | Type A + P |
| 2 | + | − | Hypermetropia and negative astigmatism | Type A + P |
| 3 | + | = | Hypermetropia | Type P |
| 4 | − | + | Myopia and positive astigmatism | Type A + M |
| 5 | − | − | Myopia and negative astigmatism | Type A + M |
| 6 | − | = | Myopia | Type M |

-continued

| Sphere | Cylinder | Defect | Treatment |
|---|---|---|---|
| 7 | = | = | Emmetropia | To be assessed |
| 8 | = | − | Negative astigmatism | To be assessed |
| 9 | = | + | Positive astigmatism | To be assessed | where:
+ indicates a dioptric value of over 0.5;
− indicates a dioptric value of below 0.5;
= indicates a dioptric value of −0.5 to +0.5.

More specifically, as regards treatment in the first six cases in the above decision table:

P type treatment: is performed by controlling the excimer laser unit to perform the following operations:

P.1) ablation of a circular corona of maximum 6 mm inside diameter, maximum 9 mm outside diameter, and of such a depth as to compensate the spherical defect;

P.2) ablation with a customized ablative pattern to eliminate higher than second-order defects, with reference to aberrometric data acquired prior to operation P.1; and P.3) if the above operations fail to achieve a coefficient of Zernike's polynomial $Z_4^0$ ranging between 0.1 and 1.0, ablation with a customized ablative pattern to obtain even greater spherical aberration.

M type treatment: is performed by controlling the excimer laser unit to perform the following operations:

M.1) ablation to such a depth as to compensate the spherical defect;

M.2) ablation with a customized ablative pattern to induce positive spherical aberration with a coefficient of Zernike's polynomial $Z_4^0$ ranging between 0.1 and 1.0.

M type treatment: is performed by controlling the excimer laser unit to perform the following operation:

A.1) cylindrical ablation, with the excimer laser unit set solely to the cylindrical defect, to bring the cylindrical defect close to zero.

As regards treatment in the last three cases in the above decision table:

Case 7: if vision of the eye improves with a positive lens, P type treatment is performed; conversely, if it improves with a negative lens, M type treatment is performed.

Cases 8 and 9: type A treatment is performed to achieve emmetropia, followed by treatment as in Case 7.

In cases (1), (2), (4) and (5), both treatments may be combined into one, if the excimer laser unit can be so programmed.

In all cases, after the operation, a check must be made to determine the coefficient of Zernike's polynomial $Z_4^0$ is within the 0.1-1.0 range. The fact that the RMS value has even increased with respect to the pre-operation value is of no importance.

The advantages of the present invention will be clear from the foregoing description.

In particular, the present invention provides for correcting presbyopia using, with appropriate control steps, the same excimer laser unit formerly only used to correct refractive defects of the human eye, such as myopia, hypermetropia, and astigmatism.

Clearly, changes may be made to what is described and illustrated herein without, however, departing from the scope of the present invention as defined in the accompanying claims.

While the foregoing description and drawings represent the present invention, it will be obvious to those skilled in the art that various changes may be made therein without departing from the true spirit and scope of the present invention.

The invention claimed is:

1. A method of controlling an excimer laser unit to perform cornea ablation to reduce presbyopia, the method comprising the step of:

a) controlling said excimer laser unit to produce on the cornea a photoablative pattern inducing a fourth-order ocular aberration;

wherein said induced fourth-order aberration is a spherical aberration; and wherein said step a) further comprises the steps of:

a1) acquiring and interpreting an aberrometric map of the eye indicating the visual defects of the eye, said visual defects comprising second-order visual defects including hypermetropia, astigmatism, and myopia, and higher-order visual defects including spherical aberration, thereby detecting a fourth-order spherical aberration;

a2) if the detected spherical aberration is negative, supplying said excimer laser unit with an overcorrect photoablative pattern that results in an induced fourth-order positive spherical aberration after treatment, the overcorrect photoablative pattern being obtained by obtaining a photoablative pattern to correct a fourth-order spherical aberration that is increased numerically in absolute value from the detected fourth-order spherical aberration;

a3) if the detected spherical aberration is positive, supplying said excimer laser unit with an overcorrect photoablative pattern that results in an induced fourth-order positive spherical aberration after treatment, the overcorrect photoablative pattern being obtained by obtaining a photoablative pattern to correct a fourth-order spherical aberration that is opposite in sign and increased numerically in absolute value from the detected fourth-order spherical aberration; and a4) controlling said excimer laser unit to implement the overcorrect photoablative pattern on said cornea.

2. The control method as claimed in claim 1;
wherein said step a) also comprises the step of:

b) controlling said excimer laser unit to perform specific photoablative treatment related to the visual defect of the eye associated with the presbyopia.

3. The control method as claimed in claim 2;
wherein said step b) comprises the steps of:

c) if the visual defect of the eye is hypermetropia, controlling said excimer laser unit to perform the following operations:

c1) ablation of a circular corona of maximum 6 mm inside diameter, maximum 9 mm outside diameter, and of such a depth as to compensate the spherical defect;

c2) ablation with a customized ablative pattern to eliminate higher than second-order defects, with reference to aberrometric data acquired prior to the operation in the preceding point; and c3) if the above operations fail to achieve a coefficient of Zernike's polynomial $Z_4^0$ ranging between 0.1 and 1.0, ablation with a customized ablative pattern to obtain even greater spherical aberration;

d) if the visual defect of the eye is hypermetropia and positive astigmatism or hypermetropia and negative astigmatism, controlling said excimer laser unit to perform the following operations:

d1) cylindrical ablation, with the excimer laser unit set solely to the cylindrical defect, to bring the cylindrical defect close to zero;
d2) ablation of a circular corona of maximum 6 mm inside diameter, maximum 9 mm outside diameter, and of such a depth as to compensate the spherical defect;
d3) ablation with a customized ablative pattern to eliminate higher than second-order defects, with reference to aberrometric data acquired prior to the operation in the preceding point; and
d4) if the above operations fail to achieve a coefficient of Zernike's polynomial $Z_4^0$ ranging between 0.1 and 1.0, ablation with a customized ablative pattern to obtain even greater spherical aberration;

e) if the visual defect of the eye is myopia, controlling said excimer laser unit to perform the following operations:
e1) ablation to such a depth as to compensate the spherical defect; and
e2) ablation with a customized ablative pattern to induce positive spherical aberration with a coefficient of Zernike's polynomial $Z_4^0$ ranging between 0.1 and 1.0;

f) if the visual defect of the eye is myopia and positive astigmatism or myopia and negative astigmatism, controlling said excimer laser unit to perform the following operations:
f1) cylindrical ablation, with the excimer laser unit set solely to the cylindrical defect, to bring the cylindrical defect close to zero;
f2) ablation to such a depth as to compensate the spherical defect; and
f3) ablation with a customized ablative pattern to induce positive spherical aberration with a coefficient of Zernike's polynomial $Z_4^0$ ranging between 0.1 and 1.0;

g) if the visual defect of the eye is emmetropia, controlling said excimer laser unit to perform:
g1) operations d2), d3) and d4), if the visual defect improves using a positive lens; and
g2) operations e1) and e2), if the visual defect improves using a negative lens;

h) if the visual defect of the eye is positive astigmatism or negative astigmatism, controlling said excimer laser unit to perform:
h1) operation d1) to achieve emmetropia;
h2) operations d2), d3) and d4), if the visual defect improves using a positive lens; and
h3) operations e1) and e2), if the visual defect improves using a negative lens.

4. The control method as claimed in claim 1, also comprising the step of:
i) controlling said excimer laser unit to form on the cornea a photoablative pattern which also corrects higher-order aberrations.

5. A controller for an excimer laser unit which performs cornea ablation to reduce presbyopia, the controller comprising:
a) first control means that controls said excimer laser unit to form on the cornea a photoablative pattern inducing a fourth-order ocular aberration;
wherein said induced fourth-order aberration is a spherical aberration; and
wherein said first control means comprise:
a1) aberrometric measuring means that acquires and interprets an aberrometric map of the eye indicating the visual defects of the eye, said visual defects comprising second-order visual defects including hypermetropia, astigmatism, and myopia, and higher-order visual defects including spherical aberration;
a2) first photoablative pattern generating means which are activated, if the detected spherical aberration is negative, to generate an overcorrect photoablative pattern that results in an induced fourth-order positive spherical aberration after treatment, the overcorrect photoablative pattern being generated by generating a photoablative pattern to correct a fourth-order spherical aberration that is numerically increased in absolute value from the fourth-order spherical aberration detected by said aberrometric measuring means;
a3) second photoablative pattern generating means which are activated, if the detected spherical aberration is positive, to generate an overcorrect photoablative pattern that results in an induced fourth-order positive spherical aberration after treatment, the overcorrect photoablative pattern being generated by generating a photoablative pattern to correct a fourth-order spherical aberration that is opposite in sign and numerically increased in absolute value from the fourth-order spherical aberration detected by said aberrometric measuring means;
a4) supply means that supplies the overcorrect photoablative pattern so generated to said excimer laser unit for implementation on said cornea.

6. The controller as claimed in claim 5;
wherein said first control means:
c) if the visual defect of the eye is hypermetropia, control said excimer laser unit to perform the following operations:
c1) ablation of a circular corona with a maximum 6 mm inside diameter and a maximum 9 mm outside diameter, and of such a depth as to compensate the spherical defect;
c2) ablation with a customized ablative pattern to eliminate higher than second-order defects, with reference to aberrometric data acquired prior to the operation in the preceding point; and
c3) if the above operations fail to achieve a coefficient of Zernike's polynomial $Z_4^0$ ranging between 0.1 and 1.0, ablation with a customized ablative pattern to obtain even greater spherical aberration;
d) if the visual defect of the eye is hypermetropia and positive astigmatism or hypermetropia and negative astigmatism, control said excimer laser unit to perform the following operations:
d1) cylindrical ablation, with the excimer laser unit set solely to the cylindrical defect, to bring the cylindrical defect close to zero;
d2) ablation of a circular corona of maximum 6 mm inside diameter, maximum 9 mm outside diameter, and of such a depth as to compensate the spherical defect;
d3) ablation with a customized ablative pattern to eliminate higher than second-order defects, with reference to aberrometric data acquired prior to the operation in the preceding point; and
d4) if the above operations fail to achieve a coefficient of Zernike's polynomial $Z_4^0$ ranging between 0.1 and 1.0, ablation with a customized ablative pattern to obtain even greater spherical aberration;
e) if the visual defect of the eye is myopia, control said excimer laser unit to perform the following operations:

e1) ablation to such a depth as to compensate the spherical defect; and e2) ablation with a customized ablative pattern to induce positive spherical aberration with a coefficient of Zernike's polynomial $Z_4^0$ ranging between 0.1 and 1.0;

f) if the visual defect of the eye is myopia and positive astigmatism or myopia and negative astigmatism, control said excimer laser unit to perform the following operations:

f1) cylindrical ablation, with the excimer laser unit set solely to the cylindrical defect, to bring the cylindrical defect close to zero;

f2) ablation to such a depth as to compensate the spherical defect; and f3) ablation with a customized ablative pattern to induce positive spherical aberration with a coefficient of Zernike's polynomial $Z_4^0$ ranging between 0.1 and 1.0;

g) if the visual defect of the eye is emmetropia, control said excimer laser unit to perform:

g1) operations d2), d3) and d4), if the visual defect improves using a positive lens; and g2) operations e1) and e2), if the visual defect improves using a negative lens;

h) if the visual defect of the eye is positive astigmatism or negative astigmatism, control said excimer laser unit to perform:

h1) operation d1) to achieve emmetropia;

h2) operations d2), d3) and d4), if the visual defect improves using a positive lens; and h3) operations e1) and e2), if the visual defect improves using a negative lens.

7. The controller as claimed in claim 5;

wherein the first control means also controls said excimer laser unit to form on the cornea a photoablative pattern which also corrects higher-order aberrations.

8. A method of reducing presbyopia, comprising:

acquiring and interpreting an aberrometric map of the eye indicating at least one visual defect of the eye, the order of said visual defect being forth-order or less; and controlling an excimer laser unit to form on the cornea a photoablative pattern inducing a fourth-order spherical ocular aberration, resulting in a forth-order spherical ocular aberration after treatment.

* * * * *